United States Patent [19]

Ando et al.

[11] Patent Number: 4,994,088

[45] Date of Patent: * Feb. 19, 1991

[54] HAIR COSMETIC COMPOSITION

[75] Inventors: Hiroshi Ando, Funabashi; Keiichi Akimoto, Sakura, both of Japan

[73] Assignee: Kao Corporation, Tokyo, Japan

[*] Notice: The portion of the term of this patent subsequent to Aug. 13, 2002 has been disclaimed.

[21] Appl. No.: 361,335

[22] Filed: Jun. 5, 1989

Related U.S. Application Data

[63] Continuation of Ser. No. 91,293, Aug. 27, 1987, abandoned, which is a continuation of Ser. No. 906,376, Sep. 12, 1986, abandoned.

[30] Foreign Application Priority Data

Sep. 30, 1985 [JP] Japan .................. 60-217514

[51] Int. Cl.$^5$ .................. A61K 7/13; A61K 7/06
[52] U.S. Cl. .................. 8/426; 8/405; 8/406; 8/428; 8/429; 424/70; 524/401; 524/547; 524/548
[58] Field of Search .................. 8/4.5, 406, 426, 428, 8/429; 424/70, 71; 524/401, 547, 548

[56] References Cited

U.S. PATENT DOCUMENTS

| | | | |
|---|---|---|---|
| 3,790,514 | 2/1974 | Elonomou | 524/401 |
| 3,836,537 | 9/1974 | Boenwinkle et al. | 524/548 |
| 4,075,131 | 2/1978 | Sterling | 424/70 |
| 4,191,674 | 3/1980 | Wismer et al. | 525/327.3 |
| 4,402,977 | 9/1983 | Grollier et al. | 424/71 |
| 4,460,758 | 7/1984 | Pfeiffer et al. | 524/547 |
| 4,520,008 | 5/1985 | Ando et al. | 424/70 |
| 4,534,892 | 8/1985 | Suzuki | 252/174.24 |
| 4,591,610 | 5/1986 | Grollier | 424/70 |
| 4,607,076 | 8/1986 | Schulz et al. | 524/548 |
| 4,622,378 | 11/1986 | Gosselink | 252/545 |
| 4,814,101 | 3/1989 | Schieferstein et al. | 252/174.23 |

FOREIGN PATENT DOCUMENTS

| | | |
|---|---|---|
| 2063671 | 6/1981 | United Kingdom . |
| 2088209 | 6/1982 | United Kingdom . |
| 2123694 | 2/1984 | United Kingdom . |
| 2136689 | 9/1984 | United Kingdom . |

OTHER PUBLICATIONS

*Cosmetics and Toiletries*, vol. 99, pp. 40–41, American Business Press, Jun. 1984.

*Primary Examiner*—Paul Lieberman
*Assistant Examiner*—Linda D. Skaling
*Attorney, Agent, or Firm*—Oblon, Spivak, McClelland, Maier & Neustadt

[57] ABSTRACT

Novel hair cosmetic compositions comprise 0.1 to 20 wt % of an amphoteric polymer which is soluble in an aqueous 10 wt % sodium chloride solution and insoluble in water at a concentration of 0.1 wt % at 20° C., and 0.1 to 30 wt % of a water-soluble inorganic salt.

The hair cosmetic compositions have good properties in terms of hair style formation and retention, and are free from objectionable feel such as stickiness. Thus, the compositions will be expected to have wide utility irrespective of the sexes and ages.

9 Claims, No Drawings

HAIR COSMETIC COMPOSITION

This application is a continuation of application Ser. No. 07/901,293, filed on Aug. 27, 1987, now abandoned.- which is a continuation of abandoned application Ser. No. 06/906,376 filed Sept. 12, 1986

BACKGROUND OF THE INVENTION

1. Field of the Invention

This invention relates to hair cosmetic compositions and more particularly, to hair cosmetic compositions which comprise amphoteric polymers and water-soluble inorganic salts whereby they exhibit a good setting performance when applied to the hair and washed with water without impeding good feel of the hair.

2. Description of the Prior Art

The hair style is one of the most important points for beauty and various beauty treatments have been conducted on the hair. For instance, transient treating processes may include a process of winding the hair about curlers and drying the curled hair, and a process of dressing the hair with an electric dryer and a brush. In order to facilitate easy dressing of the hair or keep a once dressed hair style in order, it is usual to use hair cosmetic compositions such as setting lotions, blowing agents, hair sprays and the like. The hair cosmetic compositions used for these purposes generally contain polymer materials, which are soluble in water or organic solvents such as alcohols. Examples of such materials are polyvinylpyrrolidone, vinylpyrrolidone/vinyl acetate copolymers, vinylpyrrolidne/vinyl acetate/alkylaminoacrylate copolymers, methyl vinyl ether/maleic anhydride copolymers, vinyl acetate/crotonic acid copolymers, copolymers of acrylic or methacrylic acid and acrylates or methacrylates and the like. These hair cosmetic compositions are applied onto the hair or deposited in the form of an aerosol so as to form or maintain the hair style.

However, the known hair cosmetic compositions require deposition of the polymer materials in large amounts on the hair in order to maintain the hair style. Because the polymer material deposited on the hair has a surface tension higher than the critical surface tension of the hair, it deposits on the hair in the form of islands of small pieces, so that the hair becomes very stiff to the touch. This is disadvantageous in that such hair does not show a good ready-to-comb performance.

SUMMARY OF THE INVENTION

Under these circumstances in the art, we made intensive studies on hair cosmetic compositions and, as a result, found that when hair cosmetic compositions comprising specific types of amphoteric polymers and water-soluble salts are applied onto the hair and rinsed with water, good hair style retention is ensured without impeding a good feel of the hair. The present invention was accomplished based on the above finding.

More particularly, the present invention provides a hair cosmetic composition which comprises the following ingredients (A) and (B):

(A) 0.1 to 20 wt % of an amphoteric polymer which is soluble in an aqueous 10 wt % sodium chloride solution and insoluble in water at a concentration of 0.1 wt % at 20° C.;

(B) 0.1 to 30 wt% of a water-soluble inorganic salt.

DETAILED DESCRIPTION OF THE INVENTION AND PREFERRED EMBODIMENTS

Techniques similar to those of the present invention are known including a method using, in combination, cationic polymers and amphoteric polymers (Japanese Patent Application Laid-open No. 56-92812) and a method using, in combination, anionic polymers and amphoteric polymers (Japanese Patent Application Laid-open No. 56-92813). However, these cosmetic compositions are different from the cosmetic compositions of the invention in that two types of polymers having different charges are used in combination in both references and the composition systems become more complicated.

The amphoteric polymers used in the present invention can be prepared by copolymerizing acidic vinyl monomers and basic vinyl monomers or by polymerizing amphoteric monomers, or by introducing into synthetic or natural polymers acidic groups, basic groups, both acidic and basic groups or amphoteric groups which depend on the type of synthetic or natural polymer. In all the cases, the polymers should preferably has a net electric charge of substantially zero and a molecular weight of from 500 to 5,000,000, more preferably from 5,000 to 500,000.

Typical examples of the amphoteric polymers of the invention are described below.

(1) Copolymers of acidic vinyl monomers and basic vinyl monomers

Typical copolymers are those which are obtained by copolymerizing monomer mixtures of 45 to 55 mol % of acidic vinyl monomers or their salts and 45 to 55 mol % of basic vinyl monomers or their salts in the presence of known radical polymerization initiators and in the presence or absence of known promotors at 20 to 150° C. The molar ratio used herein is intended to mean a molar ratio where the respective vinyl monomers have one acidic or basic group in one molecule. If monomers having a plurality of acidic or basic groups in one molecule are used, the molar ratio should be so controlled that the net electric charge is substantially zero.

The acidic vinyl monomers are compounds which have, in one molecule, an acidic group such as a carboxyl group, a sulfonic acid group, a phosphoric acid group or the like and a polymerizable vinyl group, and include, for example, unsaturated monobasic acids such as acrylic acid, methacrylic acid, crotonic acid, vinylbenzoic acid, 2-acrylamido-2-methylpropanesulfonic acid, styrenesulfonic acid, vinylsulfonic acid, allylsulfonic acid, methallylsulfonic acid, 3-methacrylpropanesulfonic acid and the like, and unsaturated dibasic acids such as itaconic acid, maleic acid, fumaric acid and the like and monoesters thereof. The salts of the above acidic monomers may include sodium, potassium and ammonium salts.

The basic vinyl monomers are compounds which have, in one molecule, a basic group such as a primary amino group, a secondary amino group or a tertiary amino group, and a polymerizable vinyl group and include, for example, dimethylaminoethylmethacrylate, diethylaminoethylmethacrylate, dimethylaminoethylacrylate, diethylaminoethylacrylate, dimethylaminopropylacrylate, dimethylaminopropylmethacrylamide, dimethylaminopropylacrylamide, 2-vinylpyridine, 4-vinylpyridine, dimethylallylamine, diallylmethylamine and quaternarized products thereof. The term "quaternarized product" means compounds of hydrides, methylated products, ethylated products and the like with counter anions including halogen ions such as a chlorine ion, a bromine ion and the like, a hydroxyl ion, a methylsulfate ion and the like.

The copolymerization reaction is carried out by any known techniques including bulk polymerization, aqueous solution polymerization, reverse phase suspension polymerization, precipitation polymerization and the like techniques. The reaction temperature may be in a range ordinarily used for radical polymerization and the reaction proceeds smoothly at 20 to 150° C. in the presence of a radical polymerization initiator.

The radical polymerization initiators may be any known initiators including, for example, sodium persulfate, potassium persulfate, ammonium persulfate, 2,2'-azobis(2-amidinopropane)dihydrochloride, benzoyl peroxide, hydrogen peroxide, sodium peracetate, cumene hydroperoxide, azobisisobutyronitrile and the like. Along with the polymerization initiators, promotors may be used include, for example, sodium sulfite, sodium thiosulfate, ammonium ferrous sulfate and the like. The amount of the radical polymerization initiator may vary depending on the type and is generally in the range of from 0.01 to 5 wt % of the total monomer.

Aside from the acidic and basic vinyl monomers, other third vinyl monomer components copolymerizable with the acidic and basic monomers may be added but the amount should be below 60 mol % of the total monomer composition. The third vinyl monomer components should be monovinyl compounds copolymerizalble with the aid of the radical polymerization initiator. Examples of the monovinyl compound include acrylates such as methyl acrylate, ethyl acrylate and the like, mathacrylates such as methyl methacrylate, ethyl methacrylate and the like, styrene compounds such as styrene, alpha-methylstyrene and the like, acrylamide, methacrylamide, vinyl ether, vinyl acetate and the like.

The above copolymerizable monomers can be copolymerized into a cross linked type amphoteric polymer by incorporating a suitable cross linking monomer into a reaction system of acidic vinyl monomers and basic vinyl monomers when they are polymerized. A cross linking monomer is a compound which has two or more functional groups in one molecule reacting to a vinyl group, an acid or a base. Examples of the cross linking monomer include methylenebisacrylamide, methylenebismethacrylamide, butanediol diacrylate, butanediol dimethacrylate, ethylene glycol diacrylate, ethylene glycol dimethacrylate, polyethylene glycol diacrylate, polyethylene glycol dimethacrylate, polypropylene glycol diacrylate, polypropylene glycol dimethacrylate, trimethylolpropane triacrylate, trimethylolpropane trimethacrylate, allylacrylate, allylmethacrylate, glycidyl acrylate, glycidyl methacrylate, 2-hydroxyethyl acrylate, 2-hydroxyethyl methacrylate, diacryloxyethyl phosphate, dimethacryloxyethyl phosphate, triallylcyanurate, triallylisocyanurate, divinyl benzene, diallyl maleate, polyallyl saccharose and the like. The amount of the cross linking monomer is in the range from 0.01 to 5 mol %, preferably 0.05 to 1 mol %, of the total monomer. When the cross linked type amphoteric polymer obtained is dissolved in an aqueous salt solution, the solution shows thixotropic properties. The cross linked type amphoteric polymer is thus suitably incorporated when fine particulate pigments and so on are dispersed in the hair cosmetic composition of the present invention.

(2) Polymers of amphoteric monomers

Typically, amphoteric monomers of the general formula (I) are polymerized in the presence of radical polymerization initiators at a temperature of 20 to 120° C. to obtain amphoteric polymers

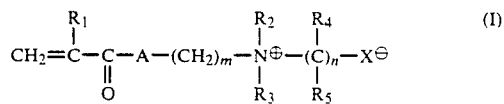

in which $R_1$, $R_4$ and $R_5$ independently represent a hydrogen atom or a methyl group, $R_2$ and $R_3$ independently represent a methyl group or an ethyl group, A is —O— or —NH—, X is —$CO_2$, —$SO_3$ or —$PHO_3$, and m and n are independently an integer of from 1 to 3.

The amphoteric monomer of the general formula (I) is prepared by reaction between an aminoalkyl ester of acrylic acid or methacrylic acid or aminoalkylamide and a lactone, a sultone or a cyclic phosphite.

Examples of the monomer include 3-dimethyl(methacroyloxyethyl)ammonium propanesulfonate, 3-dimethyl(methacroylamidopropyl)ammonium propanesulfonate and the like.

The polymerization reaction may be carried out by any known techniques such as, for example, bulk polymerization, aqueous solution polymerization, reverse phase suspension polymerization, precipitation polymerization techniques. The reaction proceeds smoothly at a reaction temperature of 20 to 150° C. in the presence of a radical polymerization initiator.

Examples of the radical polymerization initiator include sodium persulfate, potassium persulfate, ammonium persulfate, 2,2'-azobis(2-amidinopropane)dihydrochloride, benzoyl peroxide, hydrogen peroxide, sodium peracetate, cumene hydroperoxide, azobisisobutyronitrile and the like. The amount of the radical polymerization initiator may vary depending on the type of the initiator and is generaly in the range of from 0.01 to 5 wt % of the total monomer composition.

The water-soluble inorganic salts used in the practice of the invention include alkali metal, alkaline earth metal and aluminum salts of inorganic acids such as hydrochloric acid, sulfuric acid, nitric acid and the like. Preferable inorganic salts include potassium sulfate, sodium sulfate, magnesium sulfate, aluminum sulfate, potassium nitrate, sodium nitrate, magnesium nitrate, calcium nitrate, aluminum nitrate, potassium chloride, sodium chloride, magnesium chloride, potassium chloride, aluminum chloride, potassium carbonate, sodium carbonate, aluminum carbonate and the like. Of these, sodium sulfate, potassium nitrate, sodium nitrate, potassium chloride and sodium chloride are preferred.

The amount of the amphoteric polymer in the total composition is in the range of from 0.1 to 20 wt %, preferably from 0.5 to 5 wt %. Amounts less than 0.1 wt % do not show satisfactory effects, whereas amounts larger than 20 wt % are difficult to give a uniform composition. The amount of the water-soluble inorganic salt is in the range of from 0.1 to 30 wt %, preferably from 1 to 10 wt %. Below 0.1 wt %, the amphoteric polymer is difficult to dissolve. Over 30 wt %, the salt may remain on rinsing, thus impeding the feel to the touch.

The medium of the invention is substantially water or an aqueous alcohol solution containing a small amount of a lower alcohol. From 30 to 99 wt % of water is used so that total amount of the hair cosmetic composition will be 100 wt %. The pH is adjusted to from 3 to 11, preferably from 5 to 9, by the use of acids, alkalis or buffer agents. It is important to adjust the pH such that the amphoteric polymer is completely dissolved in a hair cosmetic stock solution but becomes insoluble and precipitates on dilution. For instance, when an amphoteric polymer whose net charge is almost zero at a pH of 7 is dissolved in a strongly acidic or alkaline medium, the polymer is converted to a substantially cationic or anionic polymer. If diluted, these polymers do not precipitate and thus any setting performance cannot be obtained.

The hair cosmetic composition of the present invention can be used as a hair dye-setting agent or a hair dye agent if a hair colorant such as a dyestuff and a pigment is incorporated into the composition. There are no limitations to the hair colorant. Examples of the colorant may include pigments such as titanium oxide, carbon black and the like; tar type dyestuffs such as triphenylmethane dye, azo dye, quinoline dye, xanthene dye, acridine dye, azine dye, oxazine dye, indigoid dye, anthraquinone dye, stilbene dye, thiazole dye and the like. These pigments and dyestuffs are used in an amount of from 0.1 to 5 wt % of the total hair cosmetic composition.

When the inventive cosmetic composition incorporated with the hair colorant was applied to the hair and rinsed with water, it was found that increased amount of the hair colorant was adsorbed to the hair compared with a sole use of the colorant. Thus the inventive half cosmetic composition shows an excellent coloring performance, so that hair setting and hair dyeing can be simultaneously carried out by using the inventive composition.

The cosmetic composition may be prepared into transparent liquids, lotions, emulsions, aersols (mousse) and the like without limitations. In case of the mousse, propellants used include fluorocarbons, liquefied petroleum gases and dimethyl ether, singly or in combustion, are used in an amount of from 1 to 20 wt % so that the internal pressure ranges from 2.0 to 6.0 kg/cm² G.

Aside from the above ingredients, the composition of the invention may further comprise, within amounts not impeding the effect of the invention, i.e. from 0.1 to 10 wt %, cosmetic oils and fats including: glycerides such as castor oil, cacao butter, mink oil, avogado oil, olive oil and the like; waxes such as bees wax, spermaceti, lanolin, carnauba and the like; alcohols such as cetyl alcohol, oleyl alcohol, hexadecyl alcohol, lauryl alcohol, stearyl alcohol, isostearyl alcohol, 2-octyl dodecanol, polypropylene glycol and the like; esters such as isopropyl myristate, hexyl laurate, cetyl lactate, propylene glycol monostearate, oleyl oleate, hexadecyl 2-ethylhexanoate, octyldodecyl myristate and the like; silicone derivatives such as dimethylpolysiloxane, methylphenylpolysiloxane, polyether-modified silicone oil, epoxy-modified silicone oil, amino-modified silicone oil, alkyl-modified silicone oil and the like. These oils and fats may be emulsified stably when emulsifiers are used in combination. The emulsifiers include anionic, amphoteric, cationic and nonionic surface active agents.

Preferably, a cationic surface active agent of the following general formula (II) is added to from 0.1 to 10 wt %, more preferably from 0.2 to 5 wt %, in order to ensure good conditioning

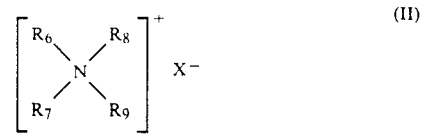

in which one or two of $R_6$, $R_7$, $R_8$ and $R_9$ independently represent a linear or branched alkyl or hydroxyalkyl group having from 8 to 22 carbon atoms and the others represent an alkyl group having from 1 to 3 carbon atoms, a hydroxyalkyl group, a benzyl group or a polyoxyethylene group whose total addition moles are 10 or below, and X represents a halogen atom or an alkylsulfate having from 1 to 2 carbon atoms.

In order to add the commercial value, perfumes or colorants may be added. In order to prevent the change of properties of the composition with time, preservatives, antioxidants and humectants such as glycerine, propylene glycol and the like may be added.

The amphoteric polymer used in the present invention shows a so-called salt-addition effect. In other words, before the product containing the polymer is applied to the hair, the polymer maintains being dissolved therein. However, once the product is applied to the hair and rinsed with water, the concentration of salt lowers, so that the polymer becomes insoluble and deposits on the hair, thus showing the setting performance.

The hair cosmetic composition of the invention has good formation and retention of a hair style without an objectionable feel such as stickiness. Thus, the cosmetic composition will be expected to have wide utility irrespective of the sexes and ages.

Synthetic examples of amphoteric polymers and examples of the invention are described.

SYNTHETIC EXAMPLE 1

143.6 g of water, 18.9 g of methacrylic acid and 34.4 g of dimethylaminoethyl methacrylate were charged, at a temperature below 20° C., into a 300 ml separatory flask equipped with an agitator, a thermometer, a reflux condenser and a dropping funnel, to which 0.063 g of ammonium persulfate and 0.026 g of sodium hydrogensulfite were added. The mixture was heated and polymerized at 35° C. for 5 hours, followed by aging at 65° C. for 30 minutes. Thereafter, the reaction solution was poured into a large amount of acetone to obtain an amphoteric polymer.

SYNTHETIC EXAMPLE 2

460 ml of hexane containing 3.0 w/v % of sorbitan monostearate was charged into a 1 liter separatory flask equipped with an agitator, a thermometer, a reflux condenser and a dropping funnel and heated for dissolution at 60° C. Thereafter, 60 g of water, 50.0 g of 2-acrylamido-2-methylpropanesulfonic acid, 37.9 g of dimethylaminoethyl methacrylate and 0.09 g of 2,2'-azobis(2-amidinopropane)dihydrochloride were further charged, followed by increasing the temperature to 62° C. and polymerization for 8 hours. After cooling, the hexane was removed by decantation, followed by drying under reduced pressure to obtain an amphoteric polymer.

SYNTHETIC EXAMPLE 3

150 g of water, 45.4 g of methacroyloxyethyltrimethylammonium chloride, 39.9 g of sodium p-styrenesulfonate, 0.063 g of ammonium persulfate, and 0.026 g of sodium hydrogensulfite were charged into a 500 ml separatory flask equipped with an agitator, a thermometer, a reflux condenser and a dropping funnel, followed by heating and polymerization at 35° C. for 5 hours and aging at 65° C. for 30 minutes. Thereafter, the reaction solution was charged into a large amount of acetone to obtain an amphoteric polymer.

SYNTHETIC EXAMPLE 4

100 g of water, 50.0 g of methacrylamidopropyltrimethylammonium chloride, 48.5 g of potassium 3-methacrylpropanesulfonate and 1.0 g of potassium peroxide were charged into a 500 ml separatory flask equipped with an agitator, a thermometer, a reflux condenser and a dropping funnel, followed by polymerizaiton at a temperature of 65° C. for 9.5 hours. After cooling, the reaction solution was charged into a large amount of acetone to obtain an amphoteric polymer.

SYNTHETIC EXAMPLE 5

5 g of 3-dimethyl(methacroyloxyethyl)ammonium propanesulfonate, 20 g of water, 0.025 g of potassium persulfate were charged into a 50 ml separatory flask equipped with an agitator, a thermometer, a reflux condenser and a dropping funnel, followed by polymerization at 65° C. for 10 hours. The reaction solution was charged into methanol to obtain an amphoteric polymer.

SYNTHETIC EXAMPLE 6

The general procedure of Example 5 was repeated using 5 g of 3-dimethyl(methacroylamidopropyl)ammonium propanesulfonate, 20 g of water and 0.025 g of potassium persulfate, thereby obtaining an amphoteric polymer.

In the following examples, the performance of hair cosmetic compositions was evaluated according to the following methods.

(1) Set retention

A hair bundle having a length of 18 cm and a weight of 1.5 g was wetted with water and then applied with 0.3 g of a hair cosmetic composition, followed by rinsing with hot water for 20 seconds, winding the bundle about a rod and natural drying. After the drying, the curled bundle was removed from the rod and suspended in a thermo-hygrostatic box of 25° C. and 98% R.H. for 30 minutes. The elogation of the curl was checked to determine a set retention in which the length of the hair immediately after the removal from the rod was determined as a set retention of 100% and the length of the original, non-curled hair (18 cm) was determined as a set retention of 0%.

(2) Feel to the touch and ready-to-brush performance

The hair bundles curled in the same manner as in (1) were organoleptically evaluated by 10 female expert panelists. The evaluation was indicated by an average value of the total points of the panelists.

| (Evaluation point) | |
|---|---|
| +3 | very good |
| +2 | good |
| +1 | fair |
| 0 | moderate |
| −1 | rather poor |
| −2 | poor |
| −3 | very poor |

EXAMPLE 1

Hair cosmetic compositions of the following formulations were prepared to determine the set retention, feel to the touch and ready-to-brush performance. Separately, the solubility of a 0.1% polymer solution in water (20° C.) and the solubility of a 0.1% polymer solution in an aqueous 10 wt % sodium chloride solution (20° C.) were also determined.

| (Formulation) | |
|---|---|
| Polymer (Table 1) | 1.5 wt % |
| Sodium chloride | 10.0 |
| Water | balance |
| | 100.0 |
| pH: 5.8–6.5 | |

TABLE 1

(Results)

| | Solubility | | | Evaluation | |
|---|---|---|---|---|---|
| Polymer (monomer) | Water (polymer: 0.1%) | Aqueous 10% NaCl solution (polymer: 0.1%) | Set retention(%) | Feel to the touch | Ready-to-brush performance |
| Dimethylaminoethyl methacrylate/methacrylic acid (Synthetic Example 1) | insoluble | soluble | 58.6 | +2.2 | +1.8 |
| Dimethylaminoethylmethacrylate/2-acrylamido-2-methylpropanesulfonic acid (Synthetic Example 2) | insoluble | soluble | 63.3 | +2.5 | +2.0 |
| Methacroyloxyethyltrimethylammonium chloride/sodium p-styrenesulfonate (Synthetic Example 3) | insoluble | soluble | 52.0 | +2.5 | +2.2 |
| Methacrylamidopropyltrimethylammonium chloride/potassium 3-methacrylpropanesulfonate (Synthetic Example 4) | insoluble | soluble | 45.0 | +2.0 | +2.3 |
| 3-dimethyl(methacroyloxyethyl)ammonium propanesulfonate (Synthetic Example 5) | insoluble | soluble | 51.0 | +2.0 | +2.0 |
| 3-dimethyl(methacroylamidopropyl)ammonium propanesulfonate (Synthetic Example 6) | insoluble | soluble | 54.8 | +1.8 | +2.4 |
| Nil (reference) | — | — | 20.0 | +0.2 | 0 |

EXAMPLE 2

The general procedure of Example 1 was repeated using an amphoteric polymer which had been prepared in accordance with Synthetic Example 2 using dimethylaminoethyl methacrylate and 2-acrylamido-2-methylpropanesulfonic acid at molar ratios indicated in Table 2, thereby preparing hair cosmetic compositions (pH 5.5 - 6.5) having such a formulation as in Example 1. These cosmetic compositions were subjected to evaluation of the performances in the same manner as in Example 1. The results are shown in Table 2.

On the other hand, another hair bundle was treated in the same manner by using a hair cosmetic composition of the same formulation as above but excluding an amphoteric polymer. The obtained hair was thin and unevenly dyed one.

TABLE 2

| Charging Molar Ratio Dimethyl aminoethyl methacrylate:2-acrylamido-2-methylpropanesulfonic acid | Solubility Water (polymer: 0.1%) | Solubility Aqueous 10% NaCl solution (polymer: 0.1%) | Set Retention (%) | Feel to the touch | Ready-to-brush performance |
|---|---|---|---|---|---|
| 50:50 | insoluble | soluble | 63.3 | +2.5 | +2.0 |
| 44:56 | insoluble | soluble | 60.0 | +2.5 | +2.2 |
| 56:44 | insoluble | soluble | 61.4 | +2.5 | +2.0 |
| 60:40 | soluble | soluble | 30.0 | +2.2 | +2.0 |
| 40:60 | soluble | soluble | 28.0 | +2.0 | +2.0 |

EXAMPLE 3

A hair cosmetic composition of the following formulation was prepared and evaluated in the same manner as in Example 1, with the result that the set retention was 51.0%, the feel to the touch was +2.6 and the ready-to-brush performance was +2.6.

| (Formulation) | |
|---|---|
| Amphoteric polymer (Synthetic Example 1) | 1.0 wt % |
| Sodium chloride | 8.0 |
| Stearyltrimethylammonium chloride | 0.3 |
| Perfume | 0.1 |
| Polyoxyethylene lauryl ether (20 E.O.) | 0.4 |
| Glycerine | 3.0 |
| Water | balance |
| pH: 6.2 | |

EXAMPLE 4

A hair cosmetic composition of the aerosol foam type of the following formulation was prepared and evaluated in the same manner as in Example 1, with the result that the set retention was 69.0%, the feel to the touch was +2.8, and the ready-to-brush performance was +2.6.

| (Formulation) | |
|---|---|
| Amphoteric polymer (Synthetic Example 2) | 2.0 wt % |
| Sodium chloride | 10.0 |
| Cetyltrimethylammonium chloride | 0.5 |
| Distearyldimethylammonium chloride | 0.3 |
| POE octyldodecyl ether (20 E.O.) | 0.5 |
| Hexadecyl alcohol | 0.3 |
| Ethanol | 5.0 |
| Perfume | 0.1 |
| Water | balance |
| Dichlorodifluoromethane | 7.0 |
| Liquefied petroleum gas (3.5 kg/cm²) | 3.0 |
| pH of Stock solution: 6.3 | |

EXAMPLE 5

A hair cosmetic composition of the following formulation was prepared and 1 g of hair bundle was immersed in it for 15 minutes. Thereafter, the hair bundle was rinsed under running water and dried by air. The thus obtained hair was recognized to be dyed deeply and evenly.

| (Formulation) | |
|---|---|
| Amphoteric polymer (Synthetic Example 2) | 1.5 wt % |
| Sodium chloride | 5.0 |
| Basic brown 76 | 0.1 |
| 0.1 N Hydrochloric acid | (adjust pH to 6.5) |
| Water | balance |

EXAMPLE 6

A hair cosmetic composition of the following formulation was prepared and applied to 1 g of hair bundle containing gray hair. After 2 minutes, the hair bundle was rinsed under running water and dried by air. No gray hair was recognized in the resulting hair bundle.

For comparison, another hair bundle containing gray hair was treated in the same manner by using a hair cosmetic composition of the same formulation as above but excluding an amphoteric polymer. As a result, the gray hair was not dyed at all.

| [Formulation] | |
|---|---|
| Amphoteric polymer (Synthetic Example 2) | 1.5 wt % |
| Sodium chloride | 5.0 |
| Polyoxyethylene(9)lauryl ether | 1.0 |
| Carbon black | 1.0 |
| Perfume | 0.1 |
| Propylene glycol | 3.0 |
| 0.1 N Hydrochloric acid | (adjust pH to 6.5) |
| Water | balance |

What is claimed is:

1. A hair cosmetic composition, consisting of:
   (A) from 0.1–20 wt. % of an amphoteric polymer prepared by copolymerizing a monomer mixture of from 45–55 mole % of at least one acidic vinyl monomer or salt thereof with 55–45 mole % of a basic vinyl monomer or salt thereof having a basic nitrogen group, said amphoteric polymer being soluble in an aqueous 10 wt. % sodium chloride solution and 0.1 wt. % of said amphoteric polymer is insoluble in water at 20° C.;
   (B) from 0.1–30 wt. % of a water-soluble inorganic salt;
   (C) from 0.1–10 wt. % of a cosmetic oil or fat;
   (D) from 0.1–10 wt. % of a quaternary ammonium surface active compound; and
   (E) from 30–99 wt. % of water or aqueous alcohol.
2. A hair cosmetic composition, consisting of:

(A) from 0.1-20 wt. % of an amphoteric polymer prepared by polymerizing an amphoteric monomer of the formula:

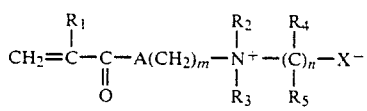
(I)

wherein $R_1$, $R_4$ and $R_5$ each independently is hydrogen or methyl, $R_2$ and $R_3$ each independently is methyl or ethyl, A is —O— or —NH—, X is —$CO_2$, —$SO_3$ or —$PHO_3$ and m and n independently are integers of from 1-3, said amphoteric polymer being soluble in an aqueous 10 wt. % sodium chloride solution and 0.1 wt. % of said amphoteric polymer is insoluble in water at 20° C.;
(B) from 0.1-30 wt. % of a water-soluble inorganic salt;
(C) from 0.1-10 wt. % of a cosmetic oil or fat;
(D) from 0.1-10 wt. % of a quaternary ammonium surface active compound; and
(E) from 30-99 wt. % of water or aqueous alcohol.

3. A hair cosmetic composition, consisting of:
(A) from 0.1-20 wt. % of an amphoteric polymer prepared by polymerizing an amphoteric monomer of the formula:

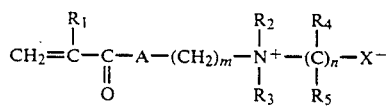
(I)

wherein $R_1$, $R_4$ and $R_5$ each independently is hydrogen or methyl, $R_2$ and $R_3$ each independently is methyl or ethyl, A is —O— or —NH—, X is —$CO_2$, —$SO_3$ or —$PHO_3$ and m and n independently are integers of from 1-3, said amphoteric polymer being soluble in an aqueous 10 wt. % sodium chloride solution and 0.1 wt. % of said amphoteric polymer is insoluble in water at 20° C.;
(B) from 0.1-30 wt. % of a water-soluble inorganic salt;
(C) from 0.1-5 wt. % of a pigment;
(D) from 0.1-10 wt. % of a cosmetic oil or fat;
(E) from 0.1-10 wt. % of a quaternary ammonium surface active compound; and
(F) from 30-99 wt. % of water or aqueous alcohol.

4. The hair cosmetic composition of claim 3, wherein said water-soluble inorganic salt (B) is an alkali metal, alkaline earth metal or auminum salt of an organic acid selected from the group consisting of potassium sulfate, sodium sulfate, magnesium sulfate, aluminum sulfte, potassium nitrate, sodium nitrate, magnesium nitrate, calcium nitrate, aluminum nitrate, potassium chloride, sodium chloride, magnesium chloride, potassium chloride, aluminum chloride, potassium carbonate, sodium carbonate and aluminum carbonate.

5. The hair cosmetic composition of claim 3, wherein said amphoteric polymer constituent (A) is present in an amount ranging from 0.5-5 wt. %.

6. The hair cosmetic composition of Claim 3, wherein the ph of the composition is within the range of from 3-11.

7. The hair cosmetic composition of Claim 3, wherein said pigment (C) is titanium oxide, carbon black or a tar based dyestuff.

8. The hair cosmetic composition of Claim 3, wherin said cosmetic oil or fat (D) is a glyceride selected from the group consisting of castor oil, cacao butter, mink oil, avogado oil, olive oil; a wax selected from the group consisting of beeswax, spermaceti, lanolin, and carnauba wax; an alcohol selected from the group consisting of cetyl alcohol, oleyl alcohol, hexadecyl alcohol, lauryl alcohol, stearyl alcohol, isostearyl alcohol, 2-octyldodecanol and polyproopylene glycol; an ester selected from the group consisting of isopropyl myristate, hexyl laurate, cetyl lactate, propylene glycol monostearate, oleyl oleate, hexadecyl 2-ethylhexanoate and octyldodecyl myristate; a silicone derivative selected from the group consisting of dimetylpolysiloxane, methylphenylpolysiloxane, a polyether-modified silicone oil, an epoxy-modified silicone oil, an amino-modified silicone oil and an alkyl modified silicone oil.

9. The hair cosmetic composition of claim 3, wherein said cationic surface active agent (E) is a compound of the formula:

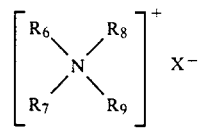
(II)

wherein one or two of the radicals $R_6$, $R_7$, $R_8$ and $R_9$ independently of each other is a linear or branched alkyl or hydroxyalkyl group of from 8-22 carbon atoms, while the remaining substituents are alkyl groups of from 1-3 carbon atoms, a hydroxyalkyl group, benzyl or a polyoxyethylene group wherein the oxyethylene units in the group is a length formed from 10 or less oxyethylene units, and X is halogen or an alkylsulfate having from 1-2 carbon atoms.

* * * * *

UNITED STATES PATENT AND TRADEMARK OFFICE
CERTIFICATE OF CORRECTION

PATENT NO. : 4,994,088
DATED : February 19, 1991
INVENTOR(S) : Hiroshi Ando et al Page 1 of 2

It is certified that error appears in the above-identified patent and that said Letters Patent is hereby corrected as shown below:

| Col. | Line | |
|---|---|---|
| 1, | 32, | delete "vinylpyrrolidne" and insert --vinylpyrrolidone--; |
| 2, | 24, | delete "has" and insert --have--; |
| 2, | 56, | delete "monosters" and insert --monoesters--; |
| 3, | 23, | delete "tors" and insert --ters that--; |
| 3, | 34, | delete "copolymerizalble" and insert --copolymerizable--; |
| 3, | 37, | delete " mathacrylates" and insert --methacrylates--; |
| 5, | 41, | delete "aersols" and insert --aerosol--; |
| 5, | 44, | delete "combustion" and insert --combination--; |
| 5, | 51, | delete "avogado" and insert --avocado--; |
| 7, | 20, | delete "polymerizaiton" and insert --polymerization--; |
| 8, | 4, | delete "elogation" and insert --elongation--; |
| 10, | 5, | delete "one"; |
| 11, | 51, | delete "auminum" and insert --aluminum--, and delete "organic" and insert --inorganic--; |
| 11, | 53, | delete "sulfte" and insert --sulfate--; |
| 12, | 16, | delete "wherin" and insert --wherein--; |
| 12, | 19, | delete "avogado" and insert --avocado--; |
| 12, | 24, | delete "polyproopylene" and insert --polypropylene--; |

UNITED STATES PATENT AND TRADEMARK OFFICE
CERTIFICATE OF CORRECTION

PATENT NO. : 4,994,088
DATED : February 19, 1991
INVENTOR(S) : HIROSHI ANDO ETAL It is certified that error appears in the above-identified patent and that said Letters Patent is hereby corrected as shown below:

Col. 12, line 50, delete "is" and insert --are--.

Signed and Sealed this

Twenty-fourth Day of November, 1992

Attest:

DOUGLAS B. COMER

Attesting Officer

Acting Commissioner of Patents and Trademarks